United States Patent [19]
Fantone et al.

[11] Patent Number: 4,784,118
[45] Date of Patent: Nov. 15, 1988

[54] OPTICAL VIEWING DEVICE

[75] Inventors: Steven D. Fantone, Lynnfield; Peter F. Costa, Cambridge; William A. Holmes, Marblehead, all of Mass.; Frederick H. Moll, San Francisco, Calif.

[73] Assignee: EndoTherapeutics, Menlo Park, Calif.

[21] Appl. No.: 43,335

[22] Filed: Apr. 28, 1987

[51] Int. Cl.⁴ .............................................. A61B 1/00
[52] U.S. Cl. ...................................... 128/6; 350/252; 350/501
[58] Field of Search ................ 128/4, 6; 350/252, 501

[56] References Cited

U.S. PATENT DOCUMENTS

| | | | |
|---|---|---|---|
| 2,482,971 | 9/1949 | Golson | 128/6 |
| 3,089,484 | 5/1963 | Hett | 128/6 |
| 3,257,902 | 6/1966 | Hopkins | 128/6 X |
| 3,297,022 | 1/1967 | Wallace | 128/6 |
| 3,414,344 | 12/1968 | Mukojima | 350/35 |
| 3,556,085 | 2/1968 | Takahashi | 128/6 |
| 3,677,262 | 7/1972 | Zukowski | 128/6 |
| 3,941,121 | 3/1976 | Olinger | 128/6 |
| 4,036,218 | 7/1977 | Yamashita et al. | 128/4 |
| 4,076,018 | 2/1978 | Heckele | 128/6 |
| 4,157,216 | 6/1979 | Plummer | 354/62 |
| 4,159,546 | 7/1979 | Shearing | 623/6 |
| 4,267,828 | 5/1981 | Matsuo | 128/6 |
| 4,273,110 | 6/1981 | Groux | 128/6 |
| 4,319,563 | 3/1982 | Kubota | 128/6 |
| 4,392,485 | 7/1983 | Hiltebrandt | 128/6 |

FOREIGN PATENT DOCUMENTS

| | | |
|---|---|---|
| 544422 | 3/1977 | U.S.S.R. |
| 683721 | 9/1979 | U.S.S.R. |
| 686725 | 9/1979 | U.S.S.R. |

*Primary Examiner*—William H. Grieb
*Attorney, Agent, or Firm*—Ciotti & Murashige, Irell & Manella

[57] ABSTRACT

An apparatus for viewing a region within a body cavity or the like. The apparatus includes an elongate light pipe having a distal end and a proximal end, which light pipe illuminates the region to be viewed adjacent the distal end of the pipe. An objective lens system is carried at that distal end which in a preferred embodiment forms a focused real image of the illuminated region. This image is transmitted to the viewer through a series of relay lenses and, at the proximal end of the apparatus, through a viewing lens system. The light pipe and the lenses are composed of a polymeric material such as styrene, polycarbonate, acrylic, or the like, and are preferably aspheric lenses.

34 Claims, 2 Drawing Sheets

OPTICAL VIEWING DEVICE

BACKGROUND OF THE INVENTION

1. Field of the Invention

This invention relates generally to optical viewing devices and more particularly concerns a disposable endoscope for use in viewing a region within a body cavity or the like.

2. Description of the Prior Art

Instruments which permit visualization of typically inaccessible areas and organs within a patient's body are known. Such optical viewing instruments, or "endoscopes," can often obviate the need for excising specimens from an internal organ of the living body for examination with a conventional microscope. Also, as disclosed in, for example, U.S. Pat. Nos. 3,677,262 to Zukowski and 4,392,485 to Hiltebrandt, endoscopes may further be provided with a means for supporting and guiding surgical instruments within a patient's body.

Structurally, endoscopes typically include a light pipe for illuminating the region to be viewed, at least one lens assembly for focusing and relaying the image of the illuminated object, and a housing for the entire assembly which is structured so as to minimize tissue damage upon examination. Examples of such endoscopes may be found in U.S. Pat. Nos. 3,089,484 to Hett, 3,257,902 to Hopkins, 3,556,085 to Takahashi, 4,267,828 to Matsuo and 4,273,110 to Groux.

There are several drawbacks in the endoscopes of the prior art to which the present invention is addressed, including the expense and complexity of the known optical viewing devices and the corresponding difficulty in volume production. The devices of the prior art incorporate expensive and carefully fabricated ground glass lenses in structures that are complicated and difficult to manufacture. Typically, as in, for example, U.S. Pat. No. 3,257,902 to Hopkins, endoscopes include a rather complicated design so as to correct for axial color aberration. Because of this, it has not been possible to make such endoscopes disposable, i.e. out of plastic materials, or easily produced in quantity.

SUMMARY OF THE INVENTION

Accordingly, it is an object of the present invention to overcome the aforementioned disadvantages of the prior art.

It is another object of the invention to provide a disposable optical device of simple and inexpensive construction.

It is still another object of the invention to provide a disposable endoscope in which the objective, relay and viewing lens assemblies are fabricated of polymeric material.

It is yet another object of the invention to provide such a disposable endoscope which is configured for direct, visual observation of an area.

It is a further object of the invention to provide such a disposable endoscope which is configured for preparation of a photographic or electronic record or display, i.e. by coupling the endoscope to a display means or to a camera or other recording means.

It is still a further object of the invention to provide a disposable endoscope as above in which the light pipe also serves as the support means for the entire optical assembly, thereby reducing the number and complexity of parts within the device.

It is still another object of the invention to provide a disposable endoscope which is sealed so as to be both airtight and watertight.

Further objects, advantages and novel features of the invention will be set forth in part in the description which follows, and in part will become apparent to those skilled in the art on examination of the following, or may be learned by practice of the invention.

In one aspect of the invention, an apparatus for viewing a region within a body cavity or the like is provided which enables direct examination of that region. The apparatus includes an elongated light pipe which is designed to direct light from a light source located at its proximal end along its length to its distal end so as to illuminate the region to be examined near its distal end. Carried at the distal end of the endoscope is an objective lens system which includes a plurality of polymeric, preferably aspheric, lens elements. These lens elements are preferably constructed so as to form a focused real image of the illuminated region prior to relay through the device, although the lens elements could also be constructed so as to form a virtual image prior to relay as well. A series of polymeric relay lenses mounted on the light pipe transmits the image to a proximal region of the light pipe, where a viewing lens system enables viewing of the relayed image. In a preferred embodiment, to maximize the length of the endoscope, the viewing lens system comprises a reversed telephoto lens assembly.

In another aspect of the invention, a light pipe having an elongate distal section extending from the pipe's distal end to a bend in the pipe adjacent the pipe's proximal end is provided wherein the elongate section includes an elongate cradlelike cavity formed therein. The cavity serves as a support means for a series of polymeric relay lenses which are aligned end-to-end within it. A sealed, elongate, substantially rigid tube encases the pipe's distal end section and the relay lenses, with the relay lenses being securely wedged between the cavity and the tube so as to maintain the lenses in axial alignment. The bend in the light pipe is preferably minimal, i.e. it should substantially eliminate any structural interference with the viewing lens assembly while minimizing loss of light at the bend.

The field of view provided by these embodiments is generally on the order of 60° to 70°, although the objective lens assembly may be constructed so as to provide a narrower or wider field of view. A Fresnel lens or other optic may be incorporated within the device at the distal end of the light pipe. Such an assembly refracts the light from the light pipe into a larger cone and thus gives a larger illuminated region. This assembly may also be used to deviate the centroid of the illumination pattern.

In order to ensure economy of manufacture, the light pipe and the objective, relay and viewing lens assemblies are preferably all fabricated of a polymeric material which lens itself to injection molding. Suitable materials include acrylics, polystyrenes, polycarbonates and styrene-acrylonitrile (SAN) copolymers.

Optionally, a means for adapting the device to be coupled to a recording or display means may be included at the proximal end of the device. With a recording means, for example, a photographic or electronic record may be made of an endoscopic examination.

DETAILED DESCRIPTION OF THE PREFERRED EMBODIMENT

Figure 1:
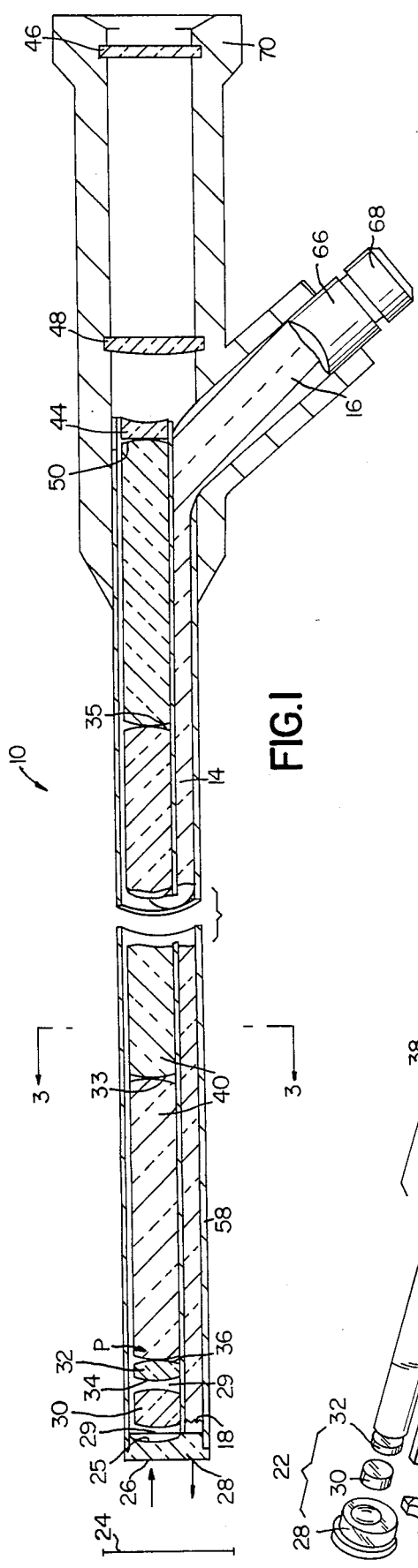
FIG. 1 is a cross-sectional side view of a preferred embodiment of an endoscope embodied by the invention.
Figure 2:
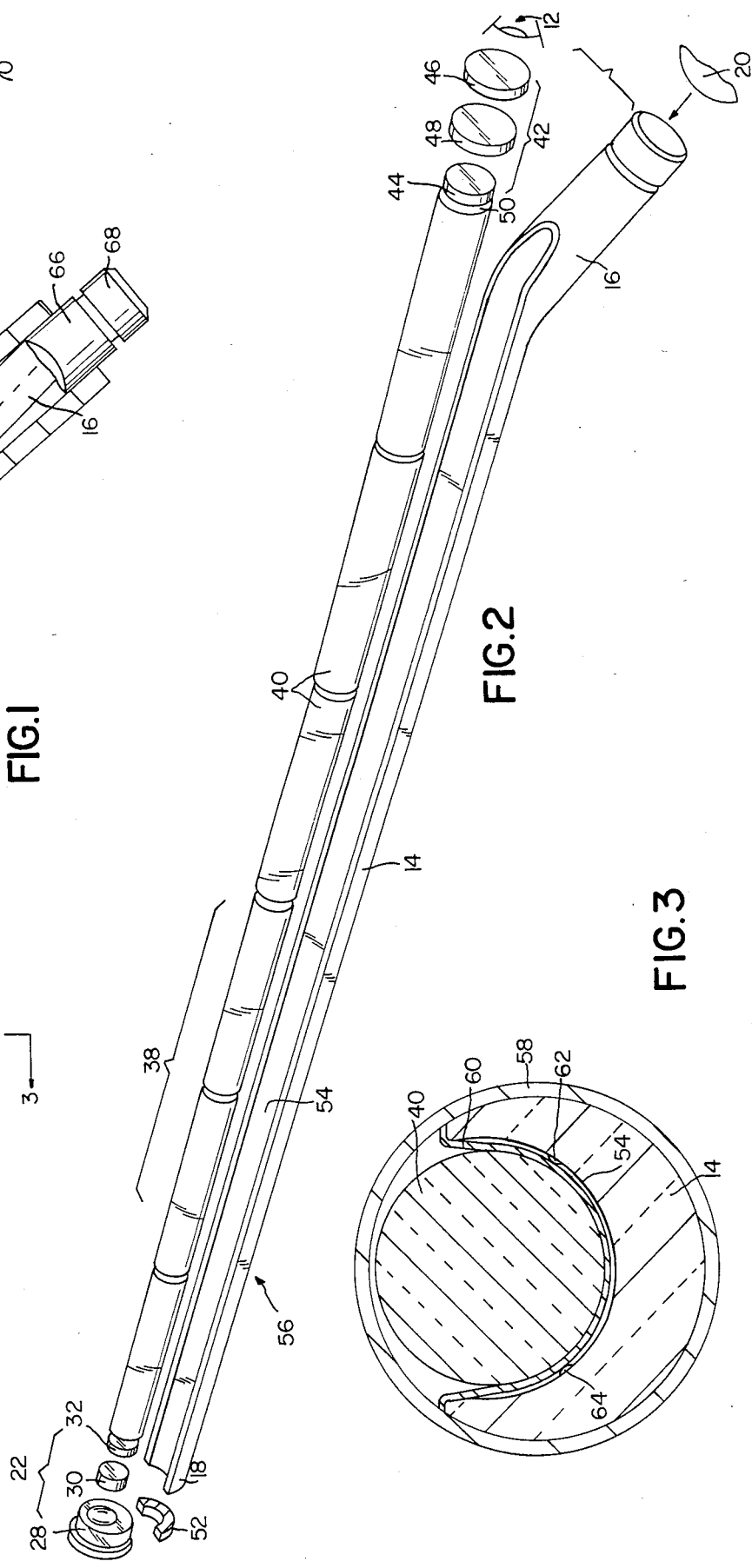
FIG. 2 is an exploded, perspective view of a preferred embodiment of the endoscope showing the series of rod lenses placed end-to-end within the molded light pipe.

Turning now to the drawings in detail, the optical viewing apparatus is shown generally at 10 and is positioned in FIGS. 1 and 2 so as to enable a viewer 12 to examine a region 24 within a body cavity or the like.

An elongate light pipe 14 disposed within the apparatus 10 is provided with a distal end 18 positioned near the region 24 to be viewed and with a proximal end 16. The light pipe directs light from a suitable light source 20 located at proximal end 16 along its length to distal end 18. Carried at the distal end of the light pipe is an objective lens system collectively designated 22 which includes a plurality of polymeric lens elements. It is preferred that the polymeric lens elements include at least one aspheric surface to improve the clarity of the image over an extended field of view. After suitable placement of the apparatus, light directed by light pipe 14 onto the region to be examined is reflected therefrom and imaged by objective lens system 22.

In the preferred embodiment illustrated in the drawings, objective lens system 22 includes the following lenses, which preferably provide a focused, real image of the illuminated region at point P, i.e. prior to relay. Surface 26 of distal negative lens 28 directly receives light reflected from the illuminated region, and is preferably planar in order to avoid change of optical power when the endoscope is immersed in a liquid. Lens 28 is preferably plano-concave as shown and aspheric on concave surface 25. The image is then processed by primary positive lens 30 which is preferably a double-convex objective lens with two aspheric surfaces. Lenses 28 and 30 together comprise a reversed telephoto lens that has a relatively short focal length and which covers a field of view on the order of 60° to 70°. Field lens 32 is located proximal to the image formed by the objective lens 30 and is preferably also a double-convex lens as shown. Like distal negative lens 28, the surfaces 34 and 36 of field lens 32 are preferably aspheric to ensure elimination of spherical and other aberration, i.e. to provide a better degree of correction and to reduce the number of lens elements needed. The primary purpose of field lens 32 is to reduce or eliminate the vignetting at the edge of the field of view. The lens is placed in the vicinity of the plane of the image. Lenses 28, 30 and 32, which together comprise the objective lens assembly herein, are made of a polymeric material such as acrylic, polystyrene, polycarbonate or SAN, preferably of a low dispersion material such as acrylic. Fabrication into suitable structures such as those illustrated may be effected by means of injection molding, conventional grinding and polishing, or diamond turning, although injection molding is the preferred method.

This placement of lenses 28, 30 and 32 at the distal end of the viewing device obviates the need for a focusing assembly, as the device is optimized to provide a focused image for areas viewed within the range of distances generally associated with therapeutic use. Outside of the typical therapeutic range, it is preferred that the device be provided with a focusing means.

Figure 4:
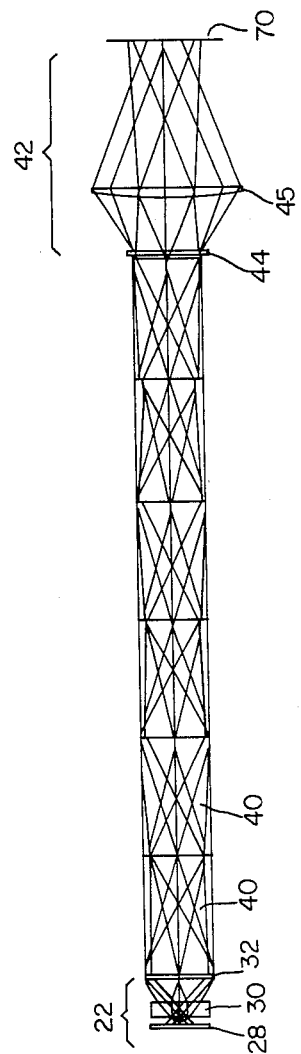
FIG. 4 is an optical layout of a preferred embodiment of the invention and illustrates ray paths and image orientation. The image is exaggerated vertically (approximately 4:1) in the y-direction for clarity.

Relay lens assembly 38 includes a plurality of rod lenses 40 arranged end-to-end so as to transmit the image provided by objective 22 through the elongate section of the apparatus to its proximal end. Like the imaging lenses, the relay lenses are fabricated from a polymeric material which lends itself to injection molding, e.g. styrene, polycarbonate, acrylic, SAN and the like. As above, low dispersion materials, acrylic in particular, are preferred. The number of relay lenses is selected so as to reduce the number of surface refractions which degrade the image while still allowing for transmission of sufficient light. For direct, visual observation of an area, the number of relay lenses is preferably an odd multiple of 2, i.e. $2(2n+1)$ where n is zero or an integer. A particularly preferred number for such an embodiment which optimizes the aforementioned considerations is six. As illustrated in FIG. 4, proper image orientation thus typically requires an odd number of symmetrically placed pairs of rod relay lenses. Alternatively, the use of an inverting prism such as a dove prism will allow for the use of an even number of relay lens pairs.

The image formed at P is collimated and refocused several times during relay, e.g., where six rod lenses are incorporated within the device, the image will be collimated and refocused three times. Because the placement of rod lenses is symmetrical, correction for lateral chromatic aberration is automatic, that is, inherent in the structure of the relay assembly. The device does not incorporate significant means of correcting for axial color, as the eye is not particularly sensitive to axial chromatic aberration; this allows for a relatively simple and inexpensive construction. The symmetry of the relay system also eliminates distortion and coma.

The individual rod lenses are difficult to make if not molded, since the radius of curvature is about half the length of the rod (thus, it would be difficult to fit several on a block for grinding). In a preferred embodiment, the rod lenses are fabricated by injection molding on standard equipment. The polymeric material is emplaced in a suitable mold and heated to at least about 350° C. A suitable mold clamping force is applied, followed by a cooling hold. Generally, a mold runner diameter about equal to the diameter of the rod lens optimizes the results obtained.

The rod lenses are preferably identical, double-convex lenses having entrant and exit refracting surfaces 33 and 35 of the same focal length. The longer the rod lenses, the darker the system appears because of a reduction in overall aperture (f-number) of the optic train. The length of the rod lenses is thus optimized to allow for transmission of sufficient light while at the same time providing for an endoscope of sufficient physical length. In a preferred embodiment, the length of each of the rod lenses is designed to be approximately equal to the focal length of the refracting surfaces. That is, for a rod lens having an index of refraction n and one surface with a focal length f, the lens will focus a distance nf away from the surface; the overall f-number of the system is thus f/d where d is the diameter of the lens. The overall f-number of the relay system is preferably optimized at between about 4 and 6. The diameter of the rod lenses is preferably between about 5 mm and about 7 mm, and the index of refraction for the materials used, e.g. acrylic or styrene, is on the order of about 1.48–1.49.

A viewing lens system 42 is housed adjacent the proximal end of the light pipe, and processes the transmitted image from the relay lens assembly 38. In one embodiment, a reverse telephoto lens assembly is used to increase the overall length of the device and the illumination of the image viewed. In such a case, viewing lens system 42 includes only two lenses, post-rod lens 44 and positive lens 48, with a window at 46. In a second embodiment, viewing lens assembly 42 includes three lenses, negative post-rod lens 44, proximal negative lens 46 (which replaces the window in the reverse telephoto assembly) and a strong positive lens 48 disposed therebetween. The post-rod lens 44 is preferably plano-concave, with the planar surface 50 facing the relay lens assembly and directly receiving the image transmitted therethrough. Like the objective and relay lenses, viewing lenses 44, 46 and 48 are fabricated from a suitable low dispersion polymeric material which lends itself to injection molding.

It should be noted at this point that applicants' endoscope—and in particular the polymeric aspheric and relay lenses—is thus completely fabricated from inexpensive materials which easily lend themselves to volume production. In a preferred embodiment, the light pipe itself is fabricated from a polymeric material such as styrene, acrylic or polycarbonate, preferably from a polymeric material with a relatively high refractive index such as polycarbonate (n~1.58).

In the embodiment described above, the field of view provided by the imaging lens assembly 22 is about 60° to about 70°. If desired, a Fresnel lens such as that shown at 52 may be provided so as to disperse light and thereby increase the uniformity of illumination within the field of view. The Fresnel lens is incorporated within the structure by placement at the distal end 18 of the light pipe, thereby refracting the light directed onto the region to be examined and providing a wider region of illumination.

Figure 3:
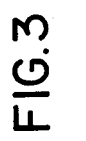
FIG. 3 is a cross-sectional view taken along the 3—3 lines of FIG. 1, and specifically illustrates the placement of one of the rod lenses within the light pipe.

Light pipe 14 is provided with an elongate cradlelike cavity 54 along its enlongate distal section 56. This cradlelike cavity provides a support means for the objective lens assembly as well as the relay lens assembly. The relay lenses 40 extend along the pipe's distal section and are arranged end-to-end as described above. A housing such as an elongate, substantially rigid tube 58 encases the light pipe 14 as well as the various lens assemblies. The tube is preferably constructed of a relatively strong, lightweight material such as aluminum, stainless steel, plastic and the like. As illustrated by FIG. 3, the relay lenses are securely wedged between cavity 54 and tube 58 so that the lenses are held in axial alignment along the length of the tube. In a preferred embodiment, the lenses of imaging lens system 22 are wedged between light pipe 14 and tube 58 in the same manner. Tube 58 is preferably sealed with adhesive, filler, or the like so as to provide an airtight, watertight seal.

The light pipe thus doubles as a mechanical support for the optic train and provides a means for easily aligning and centering the individual lens elements. The lens systems can thus be assembled without the need for complicated aligning fixtures. Although the light pipe is preferably comprised of a polymeric material which can be injection molded, it can also be fabricated from either glass or plastic fibers.

Optionally, a shielding means 60 such as dark paper, Mylar or other opaque material may be disposed between light pipe 14 and the relay lenses 40 so as to eliminate degradation of the transmitted image by light scattered from the light pipe. Shielding means 60 also helps baffle nonimaged light, i.e. light from the light pipe is prevented from entering the rod lenses directly. Spacers 62 and 64 may also be included to provide physical separation of the light pipe 14 from the relay lenses.

As may be seen in FIGS. 1 and 2, the light pipe is angled at "A" within handle 63 and becomes completely annular proximal to angle "A" where it is coupled to light source 20 by suitable means, e.g. by means of adapters 66 and 68. Although necessary to eliminate any structural interference of the proximal end of the light pipe with the viewing lens assembly, angle A is preferably minimized at about 30° or less so as to prevent loss of transmitted light.

Assembly of the endoscope is a relatively uncomplicated procedure. All lens elements except for distal negative lens 28 are initially placed in shielding paper as described and then inserted into the light pipe. Spacers 29 are provided between the objective system elements so as to ensure axial separation. Distal negative lens 28 caps the distal end of the endoscope as illustrated in FIG. 1, and the remainder of the optic train is slid toward the distal end to set axial spacing. Centering occurs upon sliding of the elements of the optic train into tube 58. Light pipe 14 and tube 58 are both, as noted above, fabricated from a strong, rigid material so as to prevent buckling during insertion and to ensure sufficient support and centering for the optic train. The pipe is allowed, however, some compression flexibility.

The invention also comprises an optic train of polymeric lens elements, preferably fabricated from a low dispersion, optical quality plastic such as acrylic. The optic train includes: (1) an objective lens assembly for forming a real image of an illuminated region that is substantially uncorrected for axial color; and (2) a relay lens assembly, similarly substantially uncorrected, which comprises an odd number of symmetrical pairs of polymeric rod lenses (or an even number used in conjunction with an inverted prism), which rod lenses are designed to relay the image along the length of the endoscope to form an image that can be observed and optionally magnified. In a preferred embodiment, the objective and relay lens assemblies are as described above and illustrated in FIG. 1.

In still another embodiment of the invention, eyepiece section 70 is provided with a means for coupling the viewing device to a display, camera, or other recording means so that a display or a photographic or other record may be made of an endoscopic examination.

Thus, as may be deduced from the above, the optical viewing device of the present invention is relatively inexpensive to fabricate; in contrast to known analogous devices, which are comprised of a number of ground glass lenses and mirrors, the present invention incorporates a large number of inexpensive polymeric components, including the light pipe as well as the relay, objective and viewing lenses. Finally, because in the apparatus of the present invention, the light pipe doubles as the support means for the system of relay lenses, the diameter and overall complexity of the device are substantially reduced.

While the invention has been described in conjunction with the preferred specific embodiments thereof, it will be understood that this description is intended to illustrate and not limit the scope of the invention, which is defined by the appended claims. It should in particular be noted that while the optical viewing device of the present invention has been described in conjunction with its use as an endoscope, other uses of the device—in viewing poorly lit and remote areas, generally—are clearly within the purview of the invention.

It is claimed:

1. Apparatus for viewing a region within a body cavity or the like, comprising:
   a light pipe having a distal end, a proximal end, and an elongate axis, designed to direct light from the proximal to the distal end to illuminate a region to be viewed near the pipe's distal end;
   carried at the distal end of the light pipe, an objective lens system comprising a plurality of polymeric objective lens elements and constructed to form an image of the region illuminated by the light pipe;
   a polymeric relay lens assembly mounted within the light pipe for relaying the image formed by the imaging system to a proximal region of the light pipe, wherein the relay lens assembly comprises symmetrical pairs of polymeric rod lenses arranged end-to-end within the light pipe, the light pipe structured to support and align the objective lens elements and the rod lenses; and
   carried adjacent such proximal region of the light pipe, a viewing lens system including a plurality of polymeric viewing lens elements constructed and arranged to allow viewing of the image relayed by the relay assembly.

2. The apparatus of claim 1, wherein the objective lens system comprises at least one aspheric surface.

3. The apparatus of claim 1, wherein the relay assembly comprises at least one aspheric surface.

4. The apparatus of claim 1, wherein the objective lens system forms a focused real image prior to relay.

5. The apparatus of claim 1, wherein a field of view between about 60° and about 70° is provided.

6. The apparatus of claim 1, wherein (i) the relay lens assembly comprises an odd number of symmetrical pairs of polymeric rod lenses or (ii) the relay lens assembly comprises an even number of symmetrical pairs of polymeric rod lenses and the viewing lens system includes an inverting prism.

7. The apparatus of claim 6, wherein the rod lenses are identical, double-convex lenses having entrant and exit refracting surfaces of substantially the same focal length.

8. The apparatus of claim 6, wherein the length of each of the rod lenses is approximately equal to the focal length of their refracting surfaces.

9. The apparatus of claim 6, wherein the rod lenses are comprised of a low dispersion polymeric material.

10. The apparatus of claim 9 wherein the low dispersion polymeric material comprises acrylic.

11. The apparatus of claim 1, wherein the viewing lens elements are comprised of a low dispersion polymeric material.

12. The apparatus of claim 1, wherein the objective lens elements are comprised of a low dispersion polymeric material.

13. The apparatus of claim 12 wheren the low dispersion polymeric material comprises acrylic.

14. The apparatus of claim 11 wherein the low dispersion polymeric material comprises acrylic.

15. The apparatus of claim 1, wherein the image viewed is formed and relayed without correction for axial chromatic aberrations.

16. The apparatus of claim 1, wherein the objective lens system includes a reversed telephoto lens assembly.

17. The apparatus of claim 1, wherein at the proximal end, the light pipe is angled away from the elongate axis.

18. The apparatus of claim 1, wherein the light pipe is angled at less than about 30° from the elongate axis.

19. The apparatus of claim 1, wherein the light pipe includes a cradlelike cavity formed in its distal end.

20. The apparatus of claim 1, wherein the light pipe and the imaging, relay and viewing lens systems supported and aligned thereby are encased within an elongate, substantially rigid tube, with the relay lenses being securely wedged between the cavity and tube so that the lenses are maintained in axial alignment along the length of the tube.

21. The apparatus of claim 1, further including a shielding means disposed between the light pipe and the relay lenses.

22. The apparatus of claim 1, wherein the light pipe is operatively connected to a Fresnel lens at its distal end.

23. The device of claim 1, wherein said tube is sealed so as to render said device both airtight and watertight.

24. The apparatus of claim 1, wherein the relay lens assembly comprises an odd number of symmetrical pairs of polymeric rod lenses.

25. The apparatus of claim 1, wherein the relay lens assembly comprises an even number of symmetrical pairs of polymeric rod lenses and the viewing apparatus includes an inverted prism.

26. An optic train useful in an endoscope, the optic train defined along a generally elongate axis and having a distal end and a proximal end, comprising:
   at the distal end of the optic train, an objective lens system including a plurality of polymeric objective lens elements;
   at the proximal end of the optic train, a viewing lens system comprising at least two polymeric viewing lens elements; and
   a series of polymeric relay lenses disposed end-to-end along the elongate axis and between the objective and viewing lens systems, wherein the relay lens assembly comprises symmetrical pairs of polymeric rod lenses placed end-to-end.

27. The optic train of claim 26, wherein the objective lens system forms a focused real image prior to relay.

28. The optic train of claim 27, wherein the rod lenses are identical, double-convex lenses having entrant and exit refracting surfaces of substantially the same focal length.

29. The optic train of claim 27, wherein the length of each of the rod lenses is approximately equal to the focal length of their refracting surfaces.

30. The optic train of claim 26, wherein (i) the relay lens assembly comprises an odd number of symmetrical pairs of polymeric rod lenses or (ii) the relay lens assembly comprises an even number of symmetrical pairs of polymeric rods lenses and the viewing lens system includes an inverted prism.

31. The optic train of claim 26, wherein the objective lens elements, the viewing lens elements and the relay lenses are comprised of a low dispersion polymeric material.

32. The optic train of claim 31, wherein the low dispersion polymeric material comprises acrylic.

33. The optic train of claim 26, wherein the relay lens assembly comprises an odd number of symmetrical pairs of polymeric rod lenses.

34. The optic train of claim 26, wherein the relay lens assembly comprises an even number of symmetrical pairs of polymeric rod lenses and the viewing apparatus includes an inverted prism.

* * * * *